(12) United States Patent
Griffin et al.

(10) Patent No.: US 11,114,197 B2
(45) Date of Patent: Sep. 7, 2021

(54) SYSTEM AND METHOD ASSOCIATED WITH DETERMINING PHYSICIAN ATTRIBUTION RELATED TO IN-PATIENT CARE USING PREDICTION-BASED ANALYSIS

(71) Applicant: THE RESEARCH FOUNDATION FOR THE STATE UNIVERSITY OF NEW YORK, Albany, NY (US)

(72) Inventors: Todd R. Griffin, St. James, NY (US); Erin J. Healy, Bethpage, NY (US); I. V. Ramakrishnan, Setauket, NY (US); Vikas Ganjigunte Ashok, Port Jefferson, NY (US)

(73) Assignee: THE RESEARCH FOUNDATION FOR THE STATE UNIVERSITY OF NEW YORK, Albany, NY (US)

(*) Notice: Subject to any disclaimer, the term of this patent is extended or adjusted under 35 U.S.C. 154(b) by 109 days.

(21) Appl. No.: 16/244,314

(22) Filed: Jan. 10, 2019

(65) Prior Publication Data
US 2019/0148007 A1   May 16, 2019

Related U.S. Application Data

(63) Continuation of application No. 14/723,619, filed on May 28, 2015, now abandoned.
(Continued)

(51) Int. Cl.
*G16H 40/20* (2018.01)
*G16H 10/60* (2018.01)

(52) U.S. Cl.
CPC ............ *G16H 40/20* (2018.01); *G16H 10/60* (2018.01)

(58) Field of Classification Search
CPC ............................ G16H 40/20; G16H 10/60
(Continued)

(56) References Cited

U.S. PATENT DOCUMENTS

| 8,515,777 B1* | 8/2013 | Rajasenan | G16H 50/30 705/2 |
| 2011/0119212 A1* | 5/2011 | De Bruin | A61B 5/00 706/12 |
| 2014/0100882 A1* | 4/2014 | Hamilton | G16H 40/20 705/3 |

* cited by examiner

*Primary Examiner* — Hiep V Nguyen
(74) *Attorney, Agent, or Firm* — Hoffmann & Baron, LLP (57) ABSTRACT

A system associated with determining physician attribution related to in-patient care based at least on prediction of attribution values associated with patient-physician attribution is disclosed. The system extracts clinical data associated with a patient from a first database, with the extracted clinical data comprising clinical information related to the patient and the clinical information including vector values indicative of clinical progress of the patient at various stages of treatment. The system stores the extracted clinical data in a second database and determines attribution values using the attribution manager with the attribution values being based on a predictive analysis using predetermined weights associated with the vector values. A training data set is generated based on learned weight values associated with the clinical progress of the patient. The system iteratively updates the vector values of the patient at least using a predictive analysis associated with the training data set. The updated vector values of the patient and the learned weight values are processed in order to cross-validate expert clinical information associated with a patient. At least one patient-physician attribution value is generated based on cross-validation of the expert clinical information and predictive
(Continued)

analysis associated with the training data set. A corresponding method and computer readable medium are also disclosed.

20 Claims, 8 Drawing Sheets

Related U.S. Application Data

(60) Provisional application No. 62/004,507, filed on May 29, 2014.
(58) Field of Classification Search
USPC .............................................. 705/3
See application file for complete search history.

Algorithm 1 Attribute

Input: Patient $p$, set of associated physicians $D_p$, notes by each physician $\vec{N}_{p,d}, d \in D_p$, feature vectors $\vec{F}_{p,d}, d \in D_p$ and a weight vector $\vec{w}$ representing the priorities of different features.

OUTPUT: Attributed Physician.

1: for all Physicians $d \in D_p$ do
2:      $Score(d) \leftarrow \vec{F}_{p,d} \cdot \vec{w}$
3: end for
4: $C_p \leftarrow \arg\max_d Score(d)$
     ▷ Resolve Ties if multiple physicians share the maximum score.
5: if $|C_p| > 1$ then
6:      for all Candidates $c \in C_p$ do
     ▷ MostRecentNote returns the date and time of the last note created by physician $c$.
7:          $DateTime(c) \leftarrow MostRecentNote(\vec{N}_{p,c})$
8:      end for
9:      $AttributedPhysician \leftarrow \arg\max_c DateTime(c)$
10: else
11:      $AttributedPhysician \leftarrow c$ such that $c \in C_p$
12: end if

FIG. 1

Algorithm 2 LearnWeights

Input: A set $P$ of patients and their corresponding data, a set of all physicians $D$.
Input: A function $\delta : P \rightarrow D$ that provides the actual attributed physician for a given patient.
Input: A function $\theta : P \times W \rightarrow D$ that predicts the attributed physician using Algorithm *Attribute* for weight vector $\vec{w} \in W$.
Input: Number of training iterations #iter, initial weight vector $\vec{w}_{init}$.
Output: Trained weight vector $\vec{w}$.

1: procedure MAIN
2:  $\quad \vec{w} \leftarrow \vec{w}_{init}$ ▷ Initialize the weight vector
  $\quad\quad\quad\quad$ ▷ $\vec{w} = (w_{oper}, w_{proc}, w_{prog}, ..., w_{other})$
3:  $\quad n \leftarrow$ #iter
4:  $\quad$ while $n > 0$ do
5:  $\quad\quad$ for all $p \in P$ do
6:  $\quad\quad\quad a \leftarrow \delta(p)$ ▷ Actual Attribution
7:  $\quad\quad\quad \hat{a} \leftarrow \theta(p, \vec{w})$ ▷ Predicted Attribtion
8:  $\quad\quad\quad \vec{w} \leftarrow UpdateWeights(p, \vec{w}, a, \hat{a}, \vec{F_{p,a}}, \vec{F_{p,\hat{a}}})$
9:  $\quad\quad$ end for
10: $\quad n \leftarrow n - 1$
11: $\quad$ end while
12: end procedure
13: procedure UPDATEWEIGHTS $(p, \vec{w}, a, \hat{a}, \vec{F_{p,a}}, \vec{F_{p,\hat{a}}})$
  $\quad\quad$ ▷ Update weights in case of incorrect preditions
14: $\quad$ if $a \neq \hat{a}$ then
  $\quad\quad$ ▷ Compute the difference between feature vectors
15: $\quad\quad \vec{g} \leftarrow \vec{F_{p,a}} - \vec{F_{p,\hat{a}}}$
  $\quad\quad\quad$ ▷ $\vec{\delta} = (\delta_{oper}, \delta_{proc}, \delta_{prog}, ..., \delta_{other})$
  $\quad\quad$ ▷ Conditional updation of feature weights
16: $\quad\quad$ if $w_{oper} + \delta_{oper} > w_{proc}$ then
17: $\quad\quad\quad w_{oper} \leftarrow w_{oper} + \delta_{oper}$
18: $\quad\quad$ end if
19: $\quad\quad$ if $w_{disch} < w_{proc} + \delta_{proc} < w_{oper}$ then
20: $\quad\quad\quad w_{proc} \leftarrow w_{proc} + \delta_{proc}$
21: $\quad\quad$ end if
22: $\quad\quad$ if $w_{admn} < w_{disch} + \delta_{disch} < w_{proc}$ then
23: $\quad\quad\quad w_{disch} \leftarrow w_{disch} + \delta_{disch}$
24: $\quad\quad$ end if
25: $\quad\quad$ if $w_{prog} < w_{admn} + \delta_{admn} < w_{disch}$ then
26: $\quad\quad\quad w_{admn} \leftarrow w_{admn} + \delta_{admn}$
27: $\quad\quad$ end if
28: $\quad\quad$ if $w_{conslt} < w_{prog} + \delta_{prog} < w_{admn}$ then
29: $\quad\quad\quad w_{prog} \leftarrow w_{prog} + \delta_{prog}$
30: $\quad\quad$ end if
31: $\quad\quad$ if $0 < w_{conslt} + \delta_{conslt} < w_{prog}$ then
32: $\quad\quad\quad w_{conslt} \leftarrow w_{conslt} + \delta_{conslt}$
33: $\quad\quad$ end if
34: $\quad\quad$ if $0 < w_{other} + \delta_{other} < w_{prog}$ then
35: $\quad\quad\quad w_{other} \leftarrow w_{other} + \delta_{other}$
36: $\quad\quad$ end if
37: $\quad$ end if
38: $\quad$ return $(w_{oper}, w_{proc}, w_{prog}, ..., w_{other})$
39: end procedure

FIG. 2

Algorithm 3 UnconstrainedLearnWeights

▷ *Input*, *Output* and *Main* same as Algorithm *LearnWeights*.

1: procedure UPDATEWEIGHTS_U($p,\vec{w},a,\hat{a},\vec{F_{p,a}},\vec{F_{p,\hat{a}}}$)
    ▷ Update weights in case of incorrect preditions
2:    if $a \neq \hat{a}$ then
    ▷ Compute the difference between feature vectors
3:        $\vec{s} \leftarrow \vec{F_{p,a}} - \vec{F_{p,\hat{a}}}$
    ▷ Unconditional updation of feature weights
4:        $\vec{w} \leftarrow \vec{w} + \vec{s}$
5:    end if
6:    return $\vec{w}$
7: end procedure

| Advanced Search | Basic Search | | | | | | | | | | | | LogOut |
|---|---|---|---|---|---|---|---|---|---|---|---|---|---|

Physician Attribution Dashboard

List of MRNs

| ▼ | < | 1 | 2 | 3 | 4 | 5 | 6 | 7 | 8 | 9 | 10 | > | ▲ |
|---|---|---|---|---|---|---|---|---|---|---|---|---|---|

| MRN | Encounter ID | Missing | Attributed Physician | Reviewed | Attribution Details |
|---|---|---|---|---|---|
| ▲ | | | | | |
| ● | ● | Yes 🔍 | ● | No | 🔍 |
| ● | ● | No 🔍 | ● | No | 🔍 |
| ● | ● | No 🔍 | ● | No | 🔍 |
| ● | ● | Yes 🔍 | ● | No | 🔍 |
| ● | ● | Yes 🔍 | ● | No | 🔍 |
| ● | ● | No 🔍 | ● | No | 🔍 |
| ● | ● | No 🔍 | ● | No | 🔍 |
| ● | ● | Yes 🔍 | ● | No | 🔍 |

FIG. 5

Physician Attribution Details

| Physician | Procedure | Progress | operative | Admission | Discharge | Consult | Others | Score |
|---|---|---|---|---|---|---|---|---|
| ▬▬ | 0 | 1 | 0 | 0 | 0 | 0 | 0 | 2.0 |
| ▬▬ | 0 | 0 | 0 | 1 | 1 | 0 | 0 | 6.6 |
| ▬▬ | 0 | 0 | 0 | 0 | 0 | 0 | 1 | 0.1 |

Status: NOT REVIEWED
Attribution: ▬▬
Attributed Department: URO
Departmental level
Attribution: ▬▬

Encounter#: ▬▬
Admin Date and Time: 2014-01-08 17:17:01
Discharge Date and Time: 2014-01-12 10:20:02

Physicians involved: [▼]

⊙ Confirm   ○ Pending

[Submit]

ID
SYSTEM AND METHOD ASSOCIATED WITH DETERMINING PHYSICIAN ATTRIBUTION RELATED TO IN-PATIENT CARE USING PREDICTION-BASED ANALYSIS

CROSS-REFERENCE TO RELATED APPLICATIONS

This application claims the benefit of U.S. application Ser. No. 14/723,619, filed on May 28, 2015 and U.S. Provisional Application No. 62/004,507, filed on May 29, 2014, the specifications of which are incorporated by reference herein in their entirety for all purposes.

FIELD OF THE DISCLOSURE

The present invention relates generally to a system and method associated with determining physician attribution related to inpatient care based at least on prediction of physician attribution. More specifically, the present invention relates to a system and method for identifying a physician responsible for administering the preponderance of care provided to a patient while receiving acute inpatient care in the hospital.

BACKGROUND OF THE DISCLOSURE

Robust, valid, and reliable physician attribution methods are essential for measuring and evaluating a physician's performance relating to the delivery of care. Robust physician performance measures using a valid attribution methodology is fundamental to identifying and implementing current and potential cost savings and quality improvement initiatives that target physician practice patterns. This is a problem and great challenge to health care organizations.

The focus of the methods and approaches to attribution reported in the literature has been on ambulatory (i.e. non-inpatient) settings such as primary care. These approaches rely on administrative and claims data to assess performance. Some approaches are centered on episodes of care that focus on health conditions from inception through evaluation and treatment (e.g. diabetes, acute sinusitis) and use attribution rules for associating episode costs to physicians from episode-claims data. Other approaches, namely health plans, profile physicians on their relative costs and use these profiles to assign physicians to cost categories. An analysis of the assorted attribution rules in the aforementioned works and their impact on the attribution measure has been reported, for example, in the *Annals of Internal Medicine*. Moreover, the recent exponential rise in hospital use of the Electronic Medical Record ("EHR") further emphasizes the need to develop and adopt automated physician attribution methods.

SUMMARY OF THE DISCLOSURE

An inventive system and method for performing physician attribution is presented. In one aspect, the invention focuses on inpatient care, which is provided to patients whose conditions require admission to a hospital. Inpatient care typically involves several physicians and the attribution problem in one aspect is to identify the physician most responsible for the patient's care. The inventive system and method leverages machine learning algorithms to automatically learn the attribution logic from a small expert-annotated dataset.

In one aspect, the present invention comprises a computational model that utilizes clinical information from a patient's EHR to retrospectively identify the physician most responsible for the patient's care in the hospital. Physician attribution provides an important data point for research on delivery of cost-effective and high quality patient care in hospitals. Unlike known systems which require expensive human-centered knowledge engineering to encode the attribution logic, in one aspect of the present invention, the logic is automatically learned from a manually-created small example set consisting of physicians attributed to patients. This approach makes the present invention highly scalable across hospitals and specialties within them. Furthermore, the precision of attribution achieved by the present invention can be over 97%. In one aspect, the inventive system and method works in real time off a daily data feed of EHRs of discharged patients.

A computer readable storage medium storing a program of instructions executable by a machine to perform one or more methods described herein also may be provided.

BRIEF DESCRIPTION OF THE DRAWINGS

These and other features, aspects, and advantages of the present invention will become better understood with regard to the following description, appended claims, and accompanying drawings wherein:

FIG. 2 illustrates an embodiment of a learning algorithm with constraints in the present invention.

DETAILED DESCRIPTION

Features in EHRs that are associated with inpatient care have been identified. Such features can include number and type of clinical notes (e.g. procedure, progress, operative, consult, etc.) and occurrences of certain entities within these notes. In cases where admission and discharge notes are unavailable, admission and discharge orders are used instead. Each feature has an associated weight that is indicative of its importance. From a patient's EHR, associated feature values are extracted for these features with respect to every physician who provided some degree of care for that patient. Accordingly, a feature refers to a name of a characteristic or attribute of an entity, such as "location", and a feature value refers to the value of the characteristic or attribute, such as "the value of feature 'location' is 'New York'". A score can be assigned to each of these physicians by computing the weighted sum of their corresponding feature values. The patient can be attributed to the physician with the highest score. Note that these weights "encode" the desired attribution logic.

In one aspect, unlike known approaches, the weights are automatically computed. Specifically, patient-physician attributions, hand constructed by a clinician with expertise in health care informatics and research, were obtained for a small dataset using information provided in the patients' EHRs. This expert-annotated data can serve as the training set for a gradient-descent based online machine learning algorithm that can be adapted to incorporate domain constraints on features. The learning algorithm can make several passes over the training set and in each pass, the learning algorithm can iterate through each example and adjust the weights, if necessary, to maximize precision. The domain constraints can be factored in when adjusting the weights. In one aspect, a web interface can allow a user to review the attribution and the feature values extracted from the EHR, correct the attribution if need be and add the corrected attribution to the training set. The addition of any corrected attribution automatically triggers the learning algorithm to recompute the new weights. The learning algorithm can thus be transparent and continuous.

The technique for inpatient attribution is described. In one aspect, the different kinds of clinical notes prepared by physicians providing care for the patient can constitute the feature set for the algorithm. Each kind or type of note can be counted and the total number of notes of each kind can be the values of features in a feature set, that is, the feature set can contain names of the features or attributes. Each feature can have a weight assigned to it that denotes its importance. Furthermore, the importance of the features in the feature set is linearly ordered. In one embodiment, the ordering knowledge can be provided by an expert clinical analyst. This order can be used in the automated learning of weights. The learned weights can be used at runtime to assign a score to each physician who provided care for the patient. Accordingly, the scores can be based on the kind and number of notes entered by each physician into the EHRs, and the relative importance of these notes. The physician with the maximum score is then attributed to the patient.

Elements of the computational model in one aspect are described. Clinical data is stored as a collection of physician notes, typically in an EHR. The following information can be obtained from each note: the patient ID for whom the note was created; the Name and Type (kind) of the note; the Date and Time when the note was entered into the patient database or EHR; and the Physician Name, ID and Department ID of the physician who prepared the note. Other information can be obtained as desired.

In particular, for each patient, several notes of different types or kinds can be prepared by various physicians during the patient's stay in inpatient care, for example during the period for which physician attribution is desired. The type of each note depends on the corresponding clinical event. For attribution purposes, in one embodiment, the following important note types can be used: Operative, Procedure, Progress, Admission, Discharge, Consult. The type of Others can be used to refer to any note type other than the aforementioned types.

More detail regarding the note types in one aspect is described. Operative notes contain details of critical operations performed in the operating room ("OR"). Information concerning any procedure that is not performed in the OR is stored in a Procedure note. Attending physicians are required to routinely evaluate a patient's health status and response to treatment and document a note detailing the patient's current condition and plan of care in Progress notes. An Admission note is created for a patient when (s)he is first admitted to the hospital. An admission note typically contains a complete medical history, details of a physical exam, the reason for hospital admission, and/or a plan of care consistent with an initial/working diagnosis. The attending physician authorizing a patient's discharge is responsible for creating a Discharge note that will include a brief summary of the health status of the patient, time of discharge, etc.

When a patient is admitted, (s)he is assigned to a clinical department based on the initial diagnosis. Depending on subsequent diagnoses and treatment, the patient may continue to stay under the care of physicians associated with the assigned department or the patient may be transferred to the care of another department. While a patient is under the care of a particular department, any note concerning that patient prepared by a physician from another department is stored as a Consult note.

Details of the features used for attribution purposes are discussed. p denotes a patient, $D_p$ refers to the set of physicians who provided inpatient care for p and d refers to a physician. For a physician d to have provided care to p means that d wrote at least one clinical note pertaining to p's care stored in patient database or EHR. The notes created by each physician $d \in D_p$ can be grouped according to their corresponding types. Therefore, the notes written by each physician for a given patient p can be represented as a vector $N_{p,d} = <N_{p,d}^{type_1}, \ldots, N_{p,d}^{type_m}>$ where each $N_{p,d}^{type_i}$, $1 \le i \le m$ denotes the set of notes of type $type_i$ created by d for p. As discussed above, in one embodiment, only seven different note types (m=7) are considered—Operative, Procedure, Progress, Admission, Discharge, Consult and Others.

The feature values are obtained by computing the number of notes of each type. Therefore, given a patient p, every physician $d \in D_p$ has an associated feature vector $$F_{p,d} = <|N_{p,d}^{type_1}|; \ldots ; |N_{p,d}^{type_m}|>.$$

TABLE 1

| PATIENT: JOHN DOE | | | | | | | |
|---|---|---|---|---|---|---|---|
| PHYSICIAN | OPR | PRC | PRG | ADM | DSC | CST | OTH |
| Dr. Dorian | 1 | 0 | 4 | 0 | 0 | 0 | 0 |
| Dr. House | 0 | 0 | 10 | 1 | 0 | 0 | 5 |
| Dr. Turk | 0 | 4 | 5 | 0 | 0 | 0 | 1 |
| Dr. Cox | 0 | 0 | 6 | 0 | 1 | 0 | 0 |

Table 1 illustrates a Feature Matrix for an example case of patient John Doe. The numerical values indicate the number of notes. That is, each column shows the number and type of note written by a particular physician. The column headings indicate the note types or kinds of: OPR=operative, PRC=procedure, PRG=progress, ADM=admission, DSC=discharge, CST=consult and OTH=other. As seen in Table I, there are 4 feature vectors corresponding to 4 physicians who provided care to the patient John Doe. As shown, for example, the feature vector <1; 0; 4; 0; 0; 0; 0> of Dr. Dorian indicates that he created one operative and four progress notes for John Doe. Similarly, the feature vector of <0; 0; 10; 1; 0; 0; 5> of Dr. House indicates he created 10 progress notes, 1 admission note and 5 other notes for John Doe.

Figure 1:
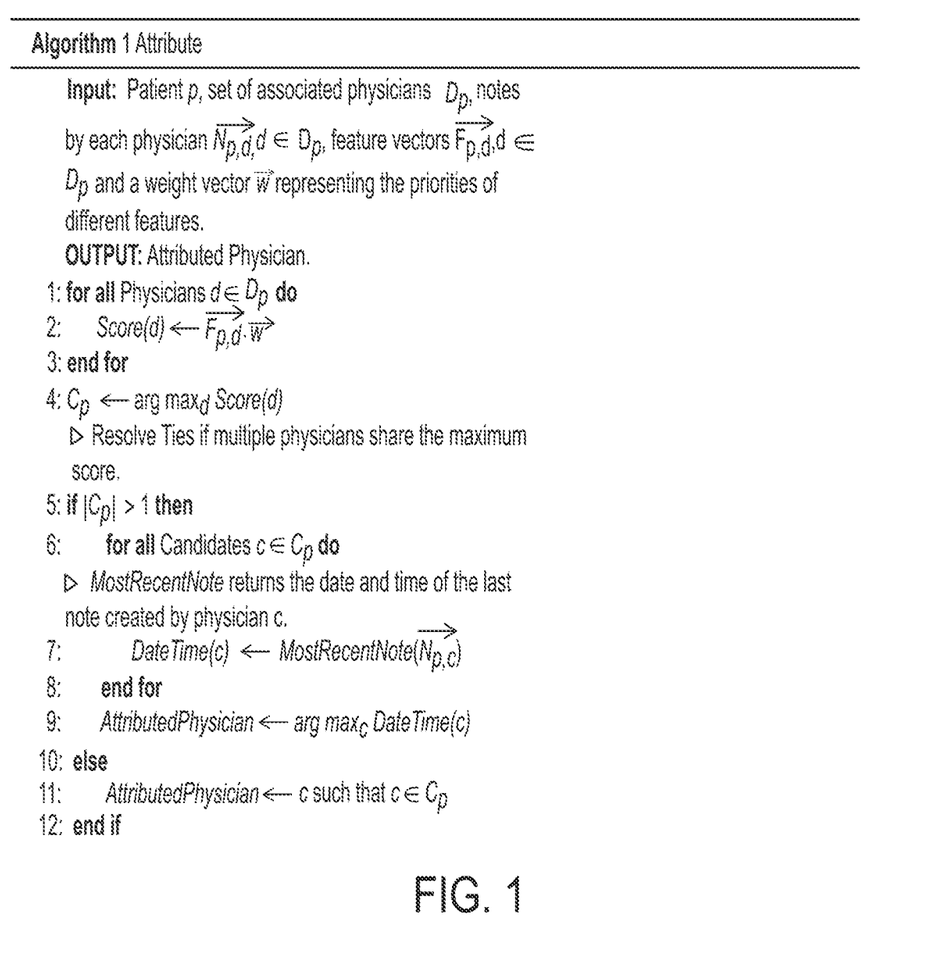
FIG. 1 illustrates an embodiment of an attribution algorithm in the present invention.

In one embodiment, physician attribution for patient p can be done using Algorithm Attribute, shown in FIG. 1. In Algorithm Attribute, the score for each physician $d \in D_p$ is computed as a scalar product of feature values and weight vectors. Different features have different priorities and the weight vector w numerically represents these priorities; the higher the priority of a note type, the greater its corresponding weight. An online learning method, such as Algorithm LearnWeights (described further below), can be employed to automatically learn these weights. For example, if the weights learned by Algorithm LearnWeights are $w_{oper}=10$, $w_{proc}=7$, $w_{prog}=2$, $w_{admn}=4$, $w_{disch}=5$, $w_{conslt}=0.4$ and $w_{other}=0.22$, then the scores computed by Algorithm Attribute for the example patient data in Table 1 are 18, 25, 38.2 and 17 for Dr. Dorian, Dr. House, Dr. Turk and Dr. Cox, respectively.

Algorithm Attribute assigns the physician with the maximum score as the attributed physician for p. In the example shown in Table 1, John Doe is attributed to Dr. Turk since Dr. Turk has the highest attribution score (38.2). However, in some cases, more than one physician may have the same maximum score. Conflicts in such cases can be resolved, for example, by attributing the patient to the physician with the most recent note, that is, the note with the highest timestamp.

TABLE 2

| ITER # | Woper | Wproc | Wprog | Wadmn | Wdisch | Wconslt | Wother |
|---|---|---|---|---|---|---|---|
| 0 | 100 | 60 | 20 | 40 | 50 | 5 | 4 |
| 5 | 100 | 74 | 23 | 36 | 38 | 6 | 2 |
| 10 | 100 | 74 | 23 | 36 | 38 | 6 | 21 |
| 15 | 100 | 74 | 23 | 37 | 39 | 6 | 2 |
| 20 | 100 | 74 | 23 | 37 | 39 | 6 | 2 |

Table 2 is an illustration of data produced using Algorithm LearnWeights. The $0^{th}$ iteration represents the initial weight vector $W_{init}$. Table 2 is discussed below.

As discussed above, the features are linearly ordered reflecting their relative importance. Specifically the sequence: Operative, Procedure, Discharge, Admission, Progress, Consult, Other, denotes the importance of the notes arranged in order of decreasing importance. In other words, Operative is more important than Procedure which is more important than Discharge and so on. Consequently the weights associated with these features are also linearly ordered to reflect the relative importance, as shown in Equation 1 ("EQ 1").

$$w_{other} < w_{conslt} < w_{prog} < w_{admn} < w_{disch} < w_{proc} < w_{oper} \quad (EQ\ 1)$$

In one aspect, the relative importance of the notes can be the domain knowledge supplied by the expert clinical informaticians. Relative importance can be determined using other techniques known to one skilled in the art.

In one embodiment, LearnWeights, shown in FIG. 2, is the supervised on-line machine learning algorithm for learning feature weights w~. LearnWeights is a gradient descent technique that has been adapted to take into account the aforementioned ordering constraint among the weights associated with the features. Other similar algorithms or techniques can be used.

LearnWeights takes four input parameters:

1) The training set P, which consists of a set of patients and associated data (list of physicians providing care, feature vectors, notes, etc).

2) A one-to-one function $\delta$: P→D. For every patient p∈P, the attributed physician d∈D, manually assigned by the expert clinical informatician.

3) A function $\theta$: P×W→D that Algorithm Attribute predicts as the attributed physician for any p∈P and a weight vector w~∈W.

4) The initial weight vector and number of iterations as the stopping condition.

In one aspect, the initials weights are randomly selected in such a way that they satisfy the ordering constraints. In Algorithm LearnWeights, EQ 1 (above) is encoded as a sequence of "If" statements in UpdateWeights LearnWeights, as shown in FIG. 2, lines 16-36. Observe that updates are made to only those weights that are consistent with respect to the ordering constraint. As is the case with other gradient descent algorithms, LearnWeights runs for a predetermined number of iterations (#iter, typically an input parameter) and updates the weights when erroneous predictions are detected.

An illustration of the iterative updating of weight vector w~ during the execution of LearnWeights is shown in Table 2 (above). An exemplary training dataset is described below. The initial weight vector $w_{init}$ (the seed) is shown in the first row ($0^{th}$ iteration) of Table 2. In the example shown in Table 2, the weights remain unchanged after the fifteenth iteration, indicating that convergence is reached between the tenth and fifteenth iterations since the weights remain unchanged after the fifteenth iteration.

Performance is typically measured in terms of prediction accuracy. Generally two datasets are used, one for training and the other for testing. The weight vector w~ learned from the training dataset is used to evaluate Algorithm Attribute on the testing dataset. Cross validation on the training dataset can be used to demonstrate robustness.

In one embodiment, the training dataset had data on 652 patients. Each of these 652 patients or cases was randomly selected from the patient database. Three schemes can be used for training the weight vector w~.

In the first scheme, called No Learning, the initial seed weights are used for evaluation and no supervised learning of w~ is done. The seed w~ can be chosen based on the clinical informatician's recommendation.

In the second scheme, called Supervised On-line Learning With Ordering Constraints, Algorithm LearnWeights is used to learn w~.

Figure 3:
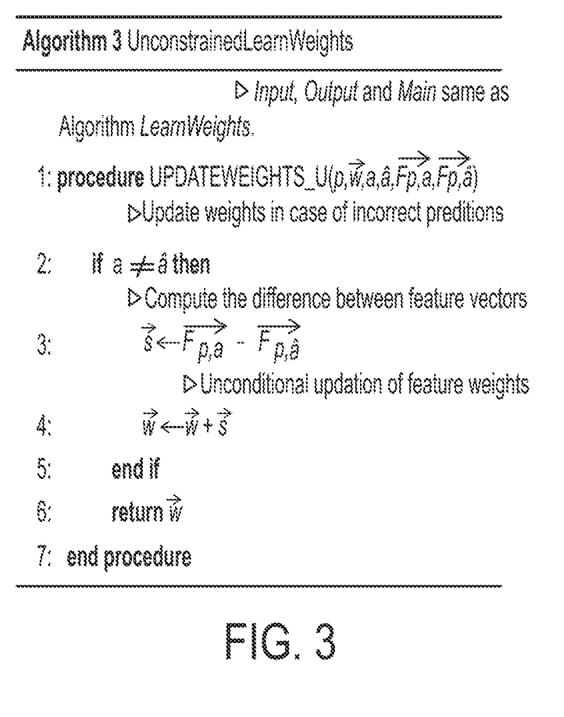
FIG. 3 illustrates an embodiment of a learning algorithm without constraints in the present invention.

In the third scheme, called Supervised Learning Without Ordering Constraints, Algorithm LearnWeights without ordering constraints is used to train w~. The Algorithm used in this scheme is shown in FIG. 3.

In one embodiment, a testing dataset comprising 270 points was used. In addition, a 5-fold cross validation was performed on the training dataset, demonstrating the effectiveness of the attribution scheme. As is known to one skilled in the art, cross validation is a technique for evaluation, typically used to assess how the results of a statistical analysis will generalize to an independent data set. A 5-fold cross validation comprises five rounds of validation where each round involves (randomly) partitioning the dataset into 5 equal sized data blocks, performing the analysis (training) on 4 blocks and validating the analysis (testing) on the remaining 1 block.

Table 3 shows prediction accuracies among the various learning methods or schemes described above. As shown in Table 3, Algorithm LearnWeights clearly outperforms the other methods.

TABLE 3

| LEARNING METHOD | CV on Training Set | Testing Set |
|---|---|---|
| No Learning | 75.4% | 70.6% |
| Algorithm LearnWeights | 98.6% | 98.1% |
| Algorithm Unconstrained LearnWeights | 89.4% | 92.1% |

Figure 4:
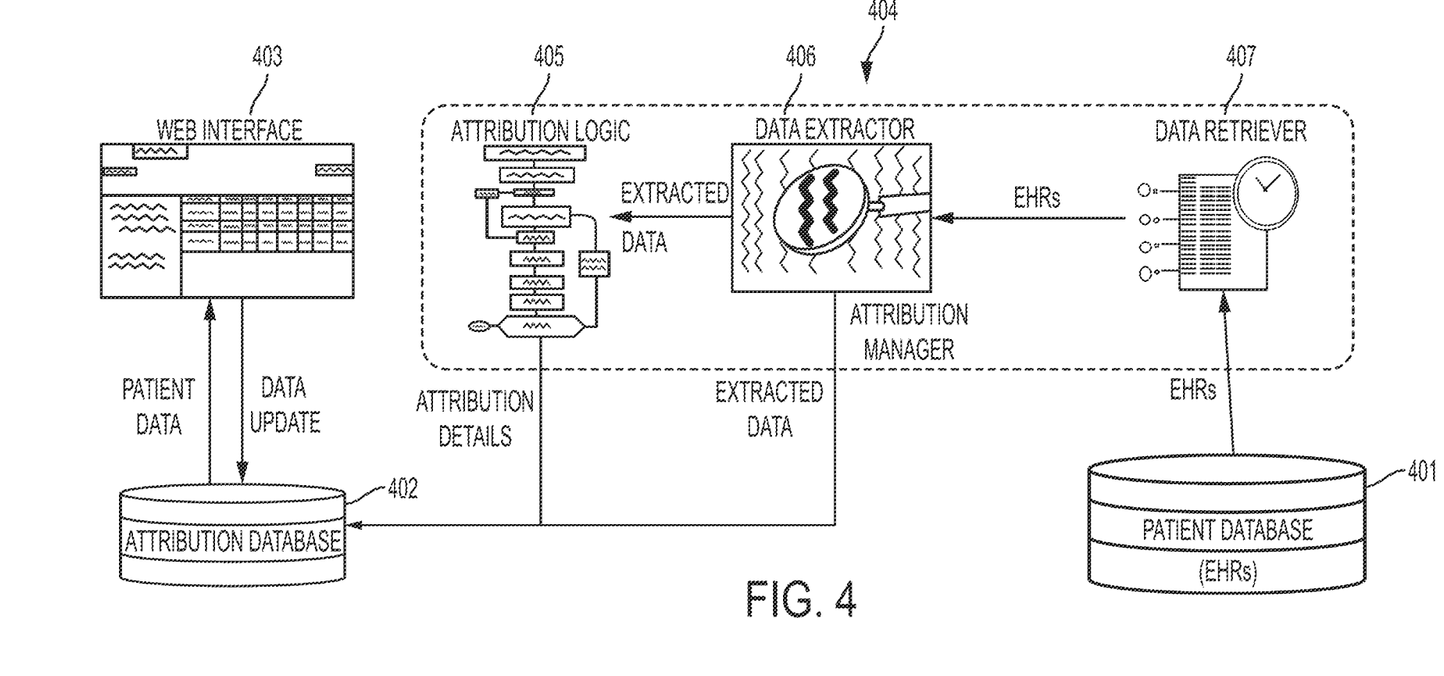
FIG. 4 illustrates a system architecture of an embodiment of the present invention.

System architecture for one embodiment of the present invention is shown in FIG. 4. As shown in FIG. 4, the system can consist of the following key components: the Patient Database 401 that has the EHRs of patients, the Attribution Database 402, a web interface 403 and an Attribution Manager 404 that executes the attribution model including the attribution logic 405 which can comprise at least Algorithms Attribute and LearnWeights, the data extractor 406 and the data retriever 407.

The Patient Database 401 can comprise EHRs of patients, including, for example, clinical notes in free text, lab reports, demographic data, etc. For the attribution task, only the clinical notes are of relevance. For any given patient, different kinds of clinical notes are prepared during his/her care. In one embodiment, the following note types are used for physician attribution in one embodiment: operative, procedure, progress, admission, discharge and consult. All these notes can be stored in Rich Text Format (RTF) or other formats known to one skilled in the art.

The Attribution Manager 404 can drive the attribution process. In one embodiment, shown in FIG. 4, the Attribution Manager 404 can comprise Data Extractor 406, Data Retriever 407, attribution logic 405, and can interface with the Attribution Database 402 and a web interface 403. The Data Retriever 407 can be scheduled to periodically retrieve fresh clinical data from the Patient Database 401. Specifically, for example, clinical notes within EHRs of all the patients discharged the previous day can be automatically pulled and passed on to the Data Extractor 406.

The Data Extractor 406 can analyze each clinical note to gather information for the attribution algorithm. This can include the type of every note, the physician who prepared each note and patient information for whom the note was written.

The attribution logic 405 can comprise two Algorithms, Attribute and LearnWeights. LearnWeights learns the weights from a training set as described above. These learned weights can be used by the attribution logic 405 to do the attribution on the data extracted by the Data Extractor 406. The physician attributed to a patient can be stored in the Attribution Database 402 along with other data described below.

In one embodiment, the Attribution Database 402 can store all attribution related data for each discharged patient. The attribution data can include the clinical notes prepared for the patient during his/her care, names and IDs of physicians who provided the care, scores assigned by Algorithm Attribute to each care provider, etc.

In one embodiment, a web interface 403 can serve as the front end to the Attribution Database 402 and a user, such as an expert clinical informatician, can interact with the Attribution Database 402 through this interface. Exemplary interface displays are shown in FIGS. 5 and 6.

Figure 5:
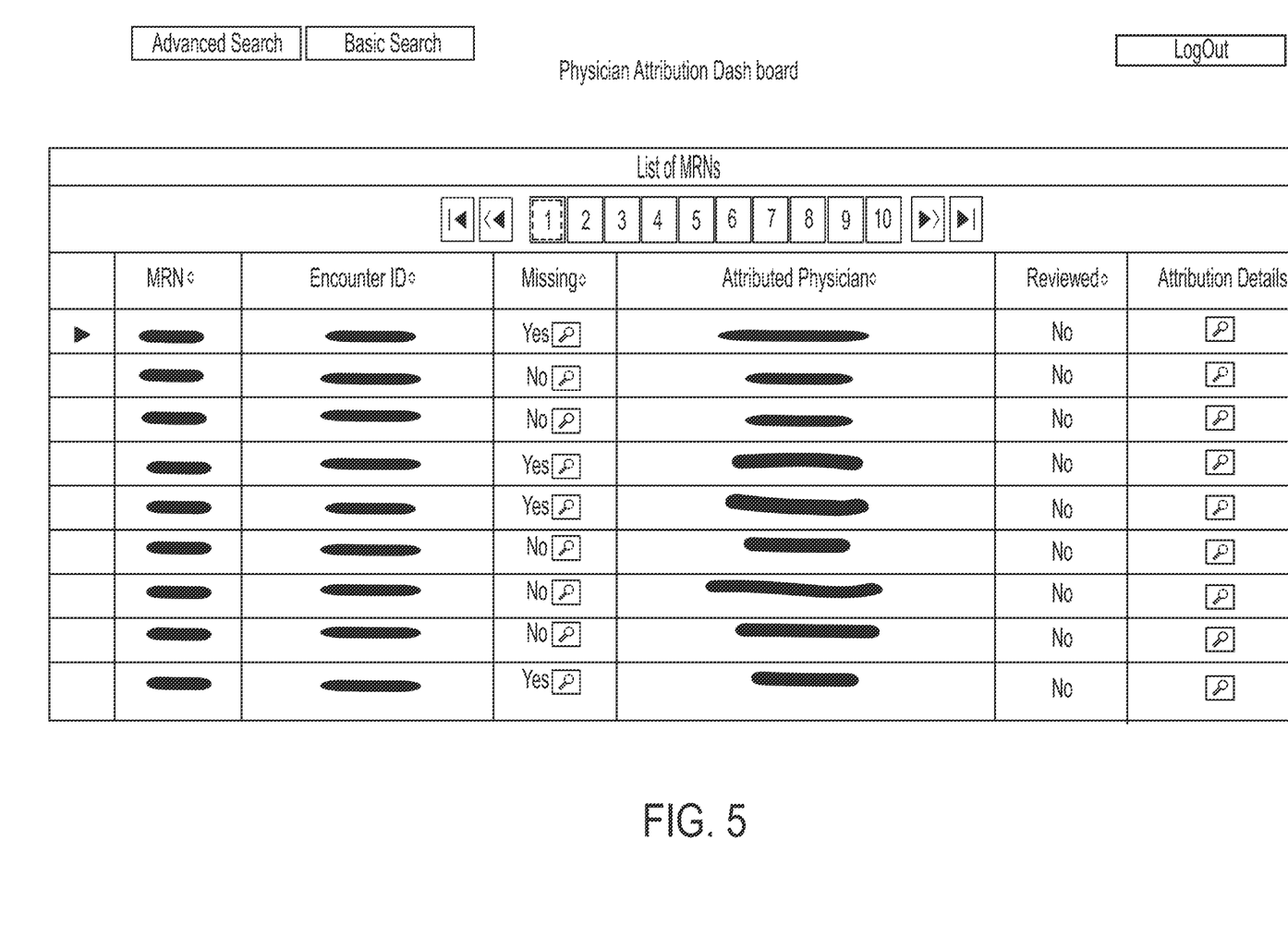
FIG. 5 illustrates an exemplary user interface in an embodiment of the present invention.

As shown in FIG. 5, the interface display can include a dashboard page with a list of patient records, where each record contains patient information, the name of the attributed physician, and a link to additional attribution details. The MRN and Encounter ID serve as identifiers for a patient. The Missing column in FIG. 5 indicates whether all the required patient information was available for attribution. The Reviewed field indicates whether the attribution value has been validated by the user, such as a clinical informatician. The dashboard page also supports filtering options, e.g. Search.

Figure 6:
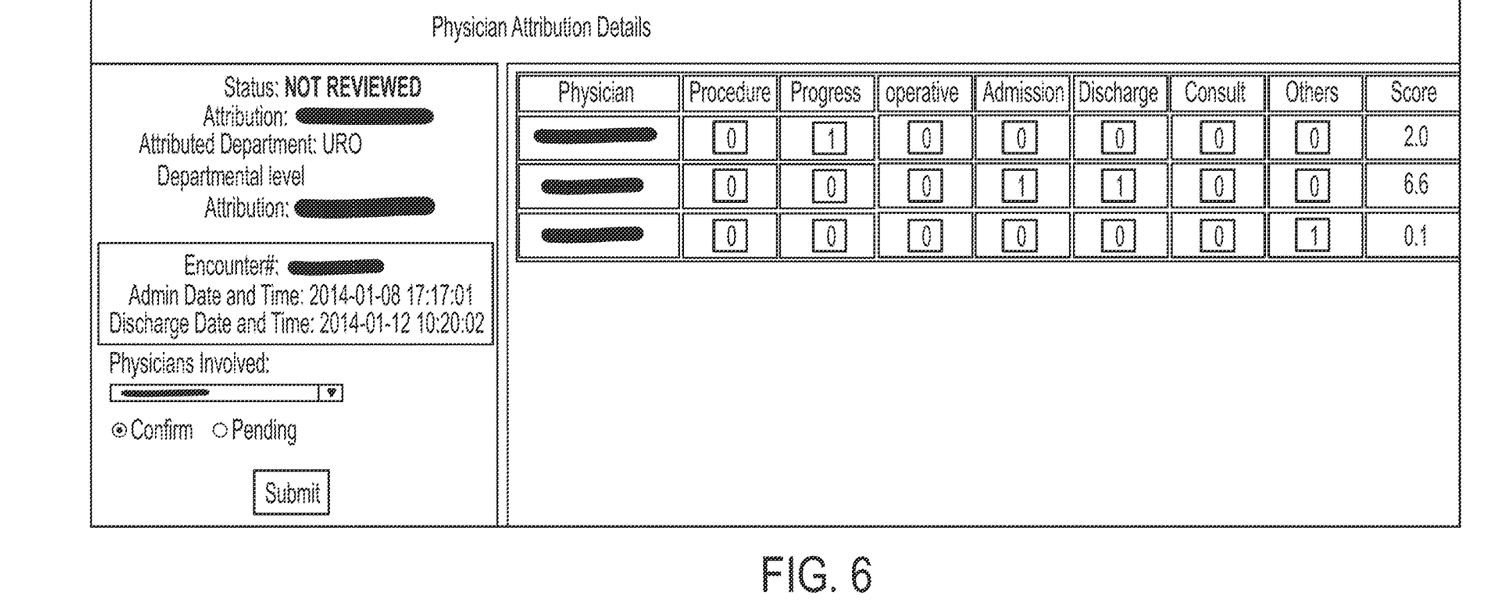
FIG. 6 illustrates another exemplary user interface in an embodiment of the present invention.

As shown in FIG. 6, the interface display can also include attribution details for each patient. The status indicates if the attribution has been validated by an expert clinical informatician or other appropriate professional. The admission and discharge date/time are also shown for convenience. These attribution details can include the list of physicians who provided care to each patient, their notes, attribution scores of each physician, etc.

Clinical notes typically are prepared by each physician who provided care. Each of the feature values, i.e., the notes in FIG. 6, is enclosed within a button that when clicked displays all the notes written by the physician. For example, in FIG. 6, clicking the button with label "1" located under the Progress column of the first row causes the appearance of an overlay that displays all the progress notes written by the physician corresponding to the first row.

The Web interface allows the user, such as an expert clinical informatician, to correct erroneous attributions. The drop-down list box labeled "Physicians Involved" shown in FIG. 6 can contain physician names to be used to correct any erroneous attributions. Specifically, a user can assign any physician in the drop-down list to be the attributed physician. This is done by selecting the appropriate physician from this drop-down list and then clicking the submit button to update the attribution information in the database. The drop-down list by default points to the attribution result produced by Algorithm Attribute. When the user wants to 'bookmark' a patient record in order to revisit it in future, (s)he can choose the option 'Pending' instead of 'Confirm'. This option sets the value of the corresponding Reviewed field in FIG. 6 to "Pending", thereby indicating to the user that the attribution is not yet confirmed. In addition, any attribution that is corrected by the user, can be added to the training set and Algorithm LearnWeights can be automatically triggered to relearn the weights. Thus (re)learning of the weights can be a continuous and seamless process.

Figure 7:
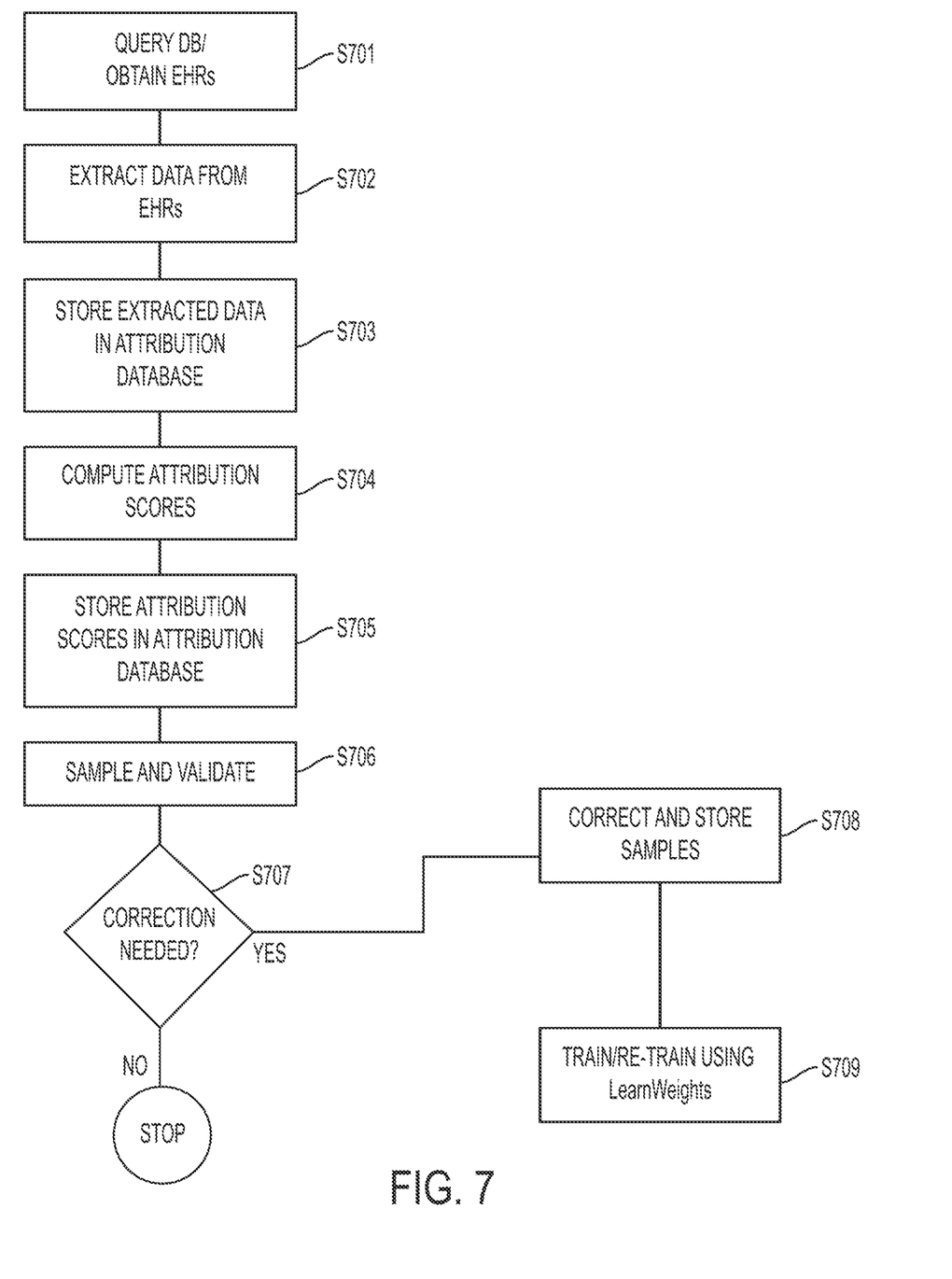
FIG. 7 illustrates an exemplary workflow in an embodiment of the present invention.

The workflow of the attribution process in one embodiment is shown in FIG. 7. In step S701, the Data Retriever periodically queries the Patient Database and retrieves EHRs of discharged patients and passes them on to the Data Extractor. In step S702, the Data Extractor extracts the patient's demographic data, details of physicians providing the care, physicians' clinical notes, etc., from the information received from the Data Retriever. In step S703, this extracted information is stored in the Attribution Database. In step S704, Algorithm Attribute uses this stored data to compute the scores of all physicians associated with each patient. In step S705, the scores are stored in the Attribution Database. In step S706, authorized users can access all the attribution information for any discharged patient at any time though the web interface, and can sample and validate the attribution results of selected records. If correction of one or more samples is needed (S707=YES), then in step S708, the appropriate samples are corrected and added to the training set. In step S709, a new cycle of Algorithm LearnWeights for re-learning new weights is performed.

If no samples need correction (S707=NO), then the process ends.

Figure 8:
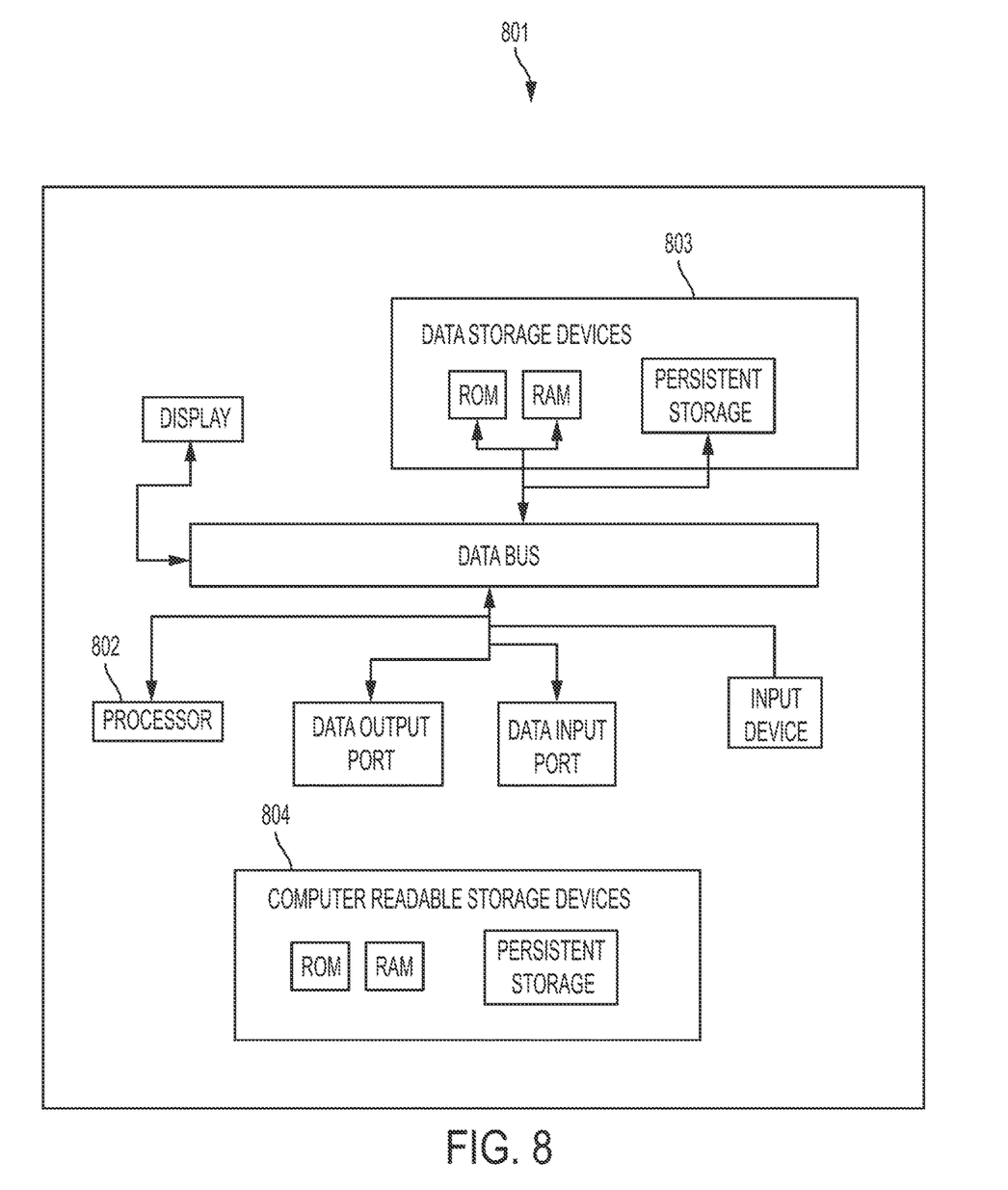
FIG. 8 is a block representation of an embodiment of the present invention.

FIG. 8 shows an embodiment of the inventive system in which a control system 801 includes a processor 802, at least one data storage device 803, such as, but not limited to, RAM, ROM and persistent storage, and an external interface. The processor 802 is configured to execute one or more programs stored in a computer readable storage device 804, which can be RAM, persistent storage or removable storage. For example, the processor 802 can execute instructions in a program that may be loaded into RAM. The processor 802 may include one or more processing units. The processor 802 can be, but is not limited to, a CPU or a GPU that can be implemented in hardware.

Various aspects of the present disclosure may be embodied as a program, software, or computer instructions embodied or stored in a computer or machine-usable or readable medium, or a group of media which causes the computer or machine to perform the steps of the method when executed on the computer, processor, and/or machine. A program storage device readable by a machine, e.g., a computer readable medium, tangibly embodying a program of instructions executable by the machine to perform various functionalities and methods described in the present disclosure is also provided, e.g., a computer program product.

The computer readable medium could be a computer readable storage device or a computer readable signal medium. A computer readable storage device may be, for example, a magnetic, optical, electronic, electromagnetic, infrared, or semiconductor system, apparatus, or device, or any suitable combination of the foregoing; however, the computer readable storage device is not limited to these examples except a computer readable storage device excludes computer readable signal medium. Additional examples of the computer readable storage device can include: a portable computer diskette, a hard disk, a magnetic storage device, a portable compact disc read-only memory (CD-ROM), a random access memory (RAM), a read-only memory (ROM), an erasable programmable read-only memory (EPROM or Flash memory), an optical storage device, or any appropriate combination of the foregoing; however, the computer readable storage device is also not limited to these examples. Any tangible medium that can contain, or store, a program for use by or in connection with an instruction execution system, apparatus, or device could be a computer readable storage device.

A computer readable signal medium may include a propagated data signal with computer readable program code embodied therein, such as, but not limited to, in baseband or as part of a carrier wave. A propagated signal may take any of a plurality of forms, including, but not limited to, electromagnetic, optical, or any suitable combination thereof. A computer readable signal medium may be any computer readable medium (exclusive of computer readable storage device) that can communicate, propagate, or transport a program for use by or in connection with a system, apparatus, or device. Program code embodied on a computer readable signal medium may be transmitted using any appropriate medium, including but not limited to wireless, wired, optical fiber cable, RF, etc., or any suitable combination of the foregoing.

The terms "a control system" and "Controller" as may be used in the present disclosure may include a variety of combinations of fixed and/or portable computer hardware, software, peripherals, and storage devices. The Controller and/or Control System may include a plurality of individual components that are networked or otherwise linked to perform collaboratively, or may include one or more stand-alone components. The hardware and software components of the Control System and/or Controller of the present disclosure may include and may be included within fixed and portable devices such as desktop, laptop, and/or server, and network of servers (cloud).

A storage device is any piece of hardware that is capable of storing information, such as, for example without limitation, data, programs, instructions, program code, and/or other suitable information, either on a temporary basis and/or a permanent basis.

In another aspect of the disclosure, an ASIC, FPGA, a PAL and PLA can be used as the processor.

The described embodiments of the present invention are intended to be illustrative rather than restrictive, and are not intended to represent every embodiment of the present invention. Various modifications and variations can be made without departing from the spirit or scope of the invention as set forth in the following claims both literally and in equivalents recognized in law.

What is claimed is:

1. A system associated with determining physician attribution related to in-patient care based at least on prediction of attribution values associated with patient-physician attribution, the system comprising:
    a memory; and
    an attribution manager, the attribution manager comprising an attribution processor connected to the memory and configured to perform operations associated with attribution analysis that include:
        receiving extracted clinical data associated with a patient from a first database, the extracted clinical data comprising clinical information related to the patient, the clinical information including one or more sets of physician notes for the patient and a number of physicians assigned to the patient, the physician notes being indicative of clinical progress of the patient at various stages of treatment;
        assigning a vector value to the one or more sets of physician notes associated with the patient and assigning a feature value to the number of physicians assigned to the patient, the physician notes being indicative of clinical progress of the patient at various stages of treatment;
        determining a weight vector value which represents a level of priority associated with each individual physician note of the one or more sets of physician notes;
        determining initial attribution values using the attribution manager, the initial attribution values being based on a predictive analysis using predetermined weights associated with the vector values and the feature value;
        generating a training data set using a machine learning algorithm, the training data set being based on learned weight values associated with the clinical progress of the patient, the machine learning algorithm iterating through each data set and adjusting the weight values to maximize precision thereof;
        iteratively updating the vector values of the patient at least using a predictive analysis associated with the training data set using the adjusted weight values;
        eliminating erroneous predictions that are detected during the predictive analysis associated with the training data set;
        determining updated weight values when the erroneous predictions are detected and eliminated during the predictive analysis in order to improve prediction accuracy;
        processing the updated vector values of the patient and the updated weight values in order to increase precision and accuracy of the clinical information associated with the patient;
        determining patient-physician attribution values based on the updated vector values and the updated weight values that increases precision of the training data set thereby cross-validating the clinical information based on elimination of erroneous predictions and improved accuracy of the predictive analysis associated with the training data set; and generating a clinical representation on a user interface device that includes validated patient-physician attribution values related to the in-patient care, the clinical representation including detailed attribution values associated with the patient, an indication of validated attribution values, and resultant attribution scores of each individual physician assigned to the patient, the attribution manager providing remote access to users over a network, through the user interface device, so that any one of the users can access data relating to the clinical representation associated with the patient.

2. The system according to claim 1, wherein the display device displays the patient and a physician attributed to the patient.

3. The system according to claim 1, the processor further performing instructions of:
sampling and validating the attribution values including attribution scores; and
correcting the predetermined weights based on the sampling and validating.

4. The system according to claim 1, further comprising:
a second database storing attribution-related data corresponding to the patient; and
a network-based user interface coupled to the second database, the network-based user interface comprising the user interface device and being configured to allow users to remotely access the second database for viewing and/or modifying the attribution-related data;
wherein the processor generates modified data using the network-based user interface.

5. The system according to claim 1, wherein the processor learns the predetermined weights based on the machine learning algorithm.

6. The system according to claim 5, further comprising computing attribution scores using predetermined weights for note types and a plurality of notes associated with the extracted data based on the machine learning algorithm.

7. The system according to claim 6, further comprising generating the clinical representation based on updated patient-physician attribution values using the attribution scores.

8. A computer-implemented method associated with determining physician attribution related to in-patient care based at least on prediction of attribution values associated with patient-physician attribution, the method comprising:
executing, on a processing device, the following operations:
receiving extracted clinical data associated with a patient from a first database, the extracted clinical data comprising clinical information related to the patient, the clinical information including one or more sets of physician notes for the patient and a number of physicians assigned to the patient, the physician notes being indicative of clinical progress of the patient at various stages of treatment;
assigning a vector value to the one or more sets of physician notes associated with the patient and assigning a feature value to the number of physicians assigned to the patient;
determining a weight vector value which represents a level of priority associated with each individual physician note of the one or more sets of physician notes;
determining initial attribution values using the attribution manager, the initial attribution values being based on a predictive analysis using predetermined weights associated with the vector values and the feature value;
generating a training data set using a machine learning algorithm, the training data set being based on learned weight values associated with the clinical progress of the patient, the learning algorithm iterating through each data set and adjusting the weight values to maximize precision thereof;
iteratively updating the vector values of the patient at least using a predictive analysis associated with the training data set using the adjusted weight values;
eliminating erroneous predictions that are detected during the predictive analysis associated with the training data set;
determining updated weight values when the erroneous predictions are detected and eliminated during the predictive analysis in order to improve prediction accuracy;
processing the updated vector values of the patient and the updated weight values in order to increase precision and accuracy of the clinical information associated with the patient;
determining patient-physician attribution values based on the updated vector values and the updated weight values that increases precision of the training data set thereby cross-validating the clinical information based on elimination of erroneous predictions and improved accuracy of the predictive analysis associated with the training data set;
generating a clinical representation on a user interface device that includes validated patient-physician attribution values related to the in-patient care, the clinical representation including detailed attribution values associated with the patient, an indication of validated attribution values, and resultant attribution scores of each individual physician assigned to the patient; and
providing remote access to users over a network, through the user interface device, so that any one of the users can access data relating to the clinical representation associated with the patient.

9. The method according to claim 8, wherein the display device displays the patient and a physician attributed to the patient data.

10. The method according to claim 8, further comprising:
sampling and validating the attribution values including scores; and
correcting the predetermined weights based on the sampling and validating.

11. The method according to claim 8, further comprising generating modified data using a network-based user interface.

12. The method according to claim 8, further comprising the processing device learning the predetermined weights based on the machine learning algorithm.

13. The method according to claim 12, further comprising computing attribution scores using predetermined weights for note types and a plurality of notes associated with the extracted data based on the machine learning algorithm.

14. The method according to claim 13, further comprising generating the clinical representation based on updated patient-physician attribution values using the attribution scores.

15. A non-transitory computer readable device storing instructions that, when executed by a processing device, cause the processing device to perform operations that include:
- receiving extracted clinical data associated with a patient from a first database, the extracted clinical data comprising clinical information related to the patient, the clinical information including one or more sets of physician notes for the patient and a number of physicians assigned to the patient, the physician notes being indicative of clinical progress of the patient at various stages of treatment;
- assigning a vector value to the one or more sets of physician notes associated with the patient and assigning a feature value to the number of physicians assigned to the patient;
- determining a weight vector value which represents a level of priority associated with each individual physician note of the one or more sets of physician notes;
- determining initial attribution values using an attribution manager, the initial attribution values being based on a predictive analysis using predetermined weights associated with the vector values and the feature value;
- generating a training data set using a machine learning algorithm, the training data set based on learned weight values associated with the clinical progress of the patient, the learning algorithm iterating through each data set and adjusting the weight values to maximize precision thereof;
- iteratively updating the vector values of the patient at least using a predictive analysis associated with the training data set using the adjusted weight values;
- eliminating erroneous predictions that are detected during the predictive analysis associated with the training data set;
- determining updated weight values when the erroneous predictions are detected and eliminated during the predictive analysis in order to improve prediction accuracy;
- processing the updated vector values of the patient and the updated weight values in order to increase precision and accuracy of the clinical information associated with the patient;
- determining patient-physician attribution values based on the updated vector values and the updated weight values that increases precision of the training data set thereby cross-validating the clinical information based on elimination of erroneous predictions and improved accuracy of the predictive analysis associated with the training data set;
- generating a clinical representation on a user interface device that includes validated patient-physician attribution values related to the in-patient care, the clinical representation including detailed attribution values associated with the patient, an indication of validated attribution values, and resultant attribution scores of each individual physician assigned to the patient; and
- providing remote access to users over a network, through the user interface device, so that any one of the users can access data relating to the clinical representation associated with the patient.

16. The non-transitory computer readable device according to claim 15, wherein the display device displays the patient and the physician attributed to the patient data.

17. The non-transitory computer readable device according to claim 15, further comprising the processing device:
- sampling and validating the attribution values including attribution scores; and
- correcting the predetermined weights based on the sampling and validating.

18. The non-transitory computer readable device according to claim 15, further comprising the processing device generating modified data using a network-based user interface.

19. The non-transitory computer readable device according to claim 15, further comprising the processing device learning the predetermined weights based on the machine learning algorithm.

20. The non-transitory computer readable device according to claim 19, further comprising the processing device computing attribution scores using predetermined weights for note types and a plurality of notes associated with the extracted data being based on the machine learning algorithm.

* * * * *